United States Patent [19]

Yamada

[11] Patent Number: 5,546,954

[45] Date of Patent: Aug. 20, 1996

[54] METHOD AND APPARATUS OF APPLYING HIGH-FREQUENCY WAVE CURRENT TO REACTIVE ELECTRO-PERMEABLE POINT OF PATIENT

[75] Inventor: Mamoru Yamada, Omiya, Japan

[73] Assignee: Yugen Kaisha Toyo Igaku, Japan

[21] Appl. No.: 317,564

[22] Filed: Oct. 4, 1994

[30] Foreign Application Priority Data

Jan. 10, 1994 [JP] Japan .................................. 6-000659

[51] Int. Cl.⁶ ................................................ A61H 39/02
[52] U.S. Cl. ................................................ 128/735
[58] Field of Search ..................... 128/639, 734, 128/735, 741; 607/147

[56] References Cited

U.S. PATENT DOCUMENTS

| | | | |
|---|---|---|---|
| 3,894,532 | 7/1975 | Morey | 128/735 |
| 3,939,841 | 2/1976 | Dohring et al. | |
| 4,016,870 | 4/1977 | Lock | 128/735 |
| 4,052,978 | 10/1977 | Eugenio | 128/735 |
| 4,095,601 | 6/1978 | Aufanc | 607/147 |
| 4,408,617 | 10/1983 | Auguste | 128/735 |
| 5,012,816 | 5/1991 | Lederer | 128/735 |
| 5,385,150 | 1/1995 | Ishikawa | 128/735 |

FOREIGN PATENT DOCUMENTS

| | | |
|---|---|---|
| 2634401 | 1/1978 | Germany . |
| 3044837 | 9/1982 | Germany . |
| 4006916 | 7/1991 | Germany . |

OTHER PUBLICATIONS

Yamamoto, T., et al., "Measure of Low–Resistance Points on the Skin by Dry Roller Electrodes", I.E.E.E. Transactions on Biomedical Engineering, vol. 35, No. 3, Mar. 1988.

*Primary Examiner*—Max Hindenburg
*Attorney, Agent, or Firm*—Ronald P. Kananen

[57] ABSTRACT

A method of doing medical treatment to a patient includes applying high-frequency wave current to a reactive electro-permeable point of a patient for a predtermined time and is implemented such that one of two electrodes is contacted with an acupuncture needle inserted at a reactive electro-permeable point while the other electrode is attached on a portion of the patient relatively near the one electrode, and high-frequency wave current is then flowed between the electrodes. The method further includes searching objective reactive electro-permeable points.

15 Claims, 5 Drawing Sheets

FIG.3A FIG.3B
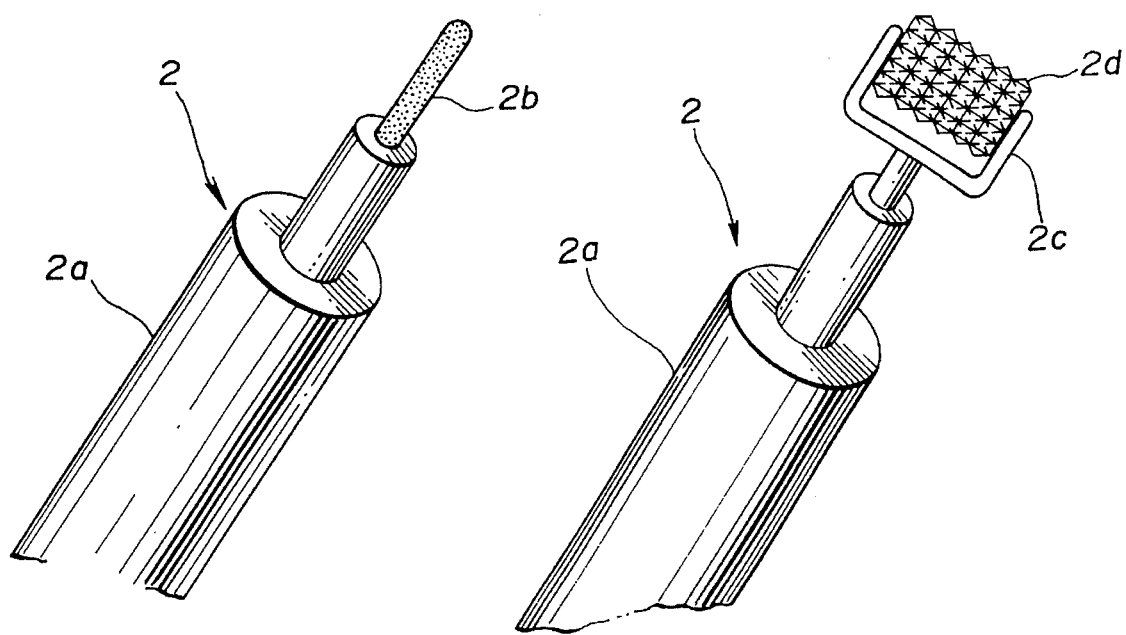

BACK  FRONT

BACK  FRONT

FIG.4C
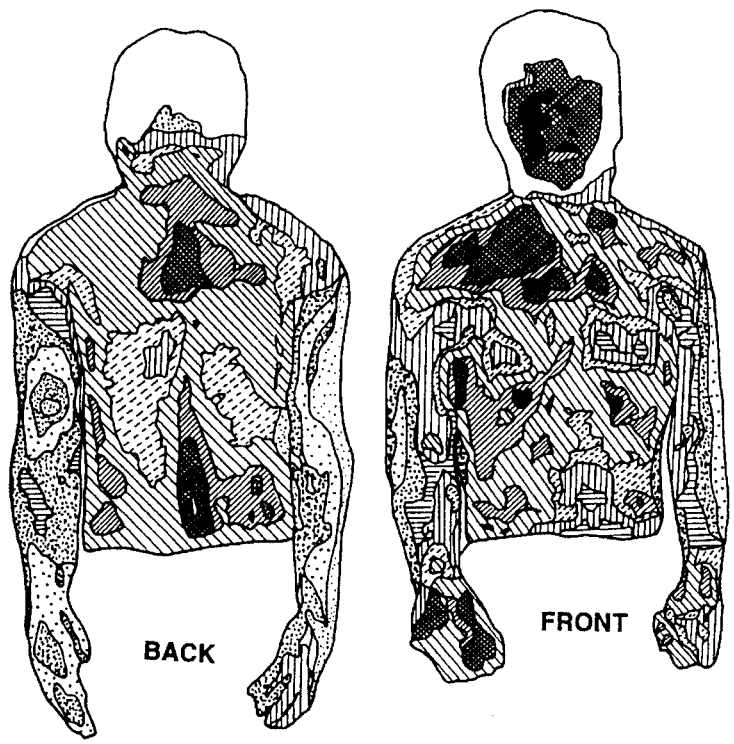
BACK  FRONT
FIG.4D
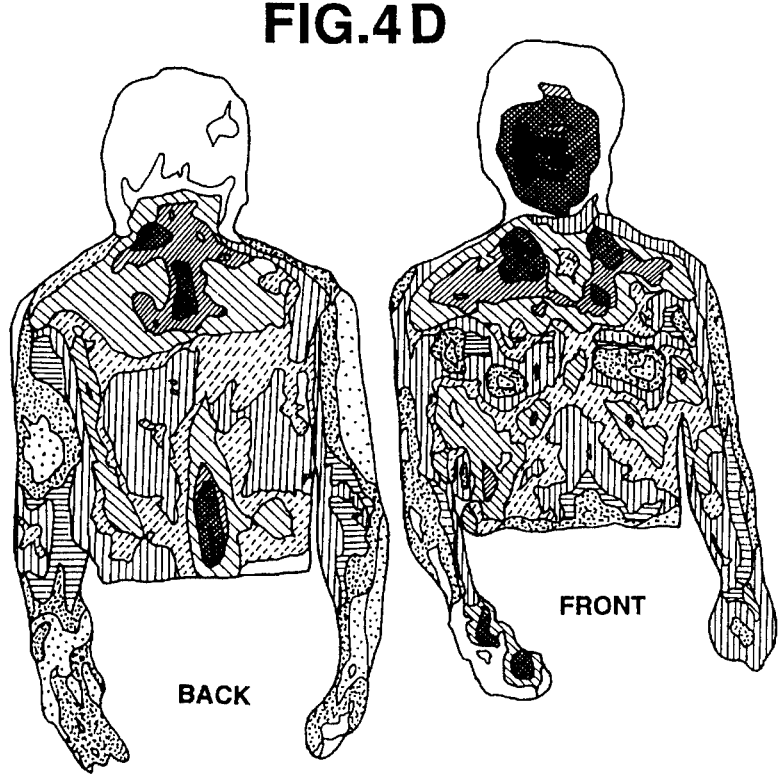
BACK  FRONT
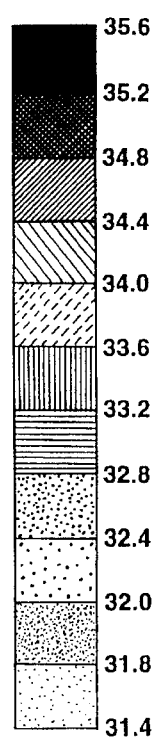
35.6
35.2
34.8
34.4
34.0
33.6
33.2
32.8
32.4
32.0
31.8
31.4

METHOD AND APPARATUS OF APPLYING HIGH-FREQUENCY WAVE CURRENT TO REACTIVE ELECTRO-PERMEABLE POINT OF PATIENT

BACKGROUND OF THE INVENTION

1. Field of the Invention

The present invention relates to a method and apparatus of doing medical treatments by applying high-frequency wave current to reactive electro-permeable points of a patient.

2. Description of the Prior Art

Hitherto, various health maintenance techniques have been proposed and in practical use in order to accelerate hemokinesis and/or relieve stiff shoulders and the like. One such technique is arranged to involuntarily move muscles of a patient by connecting an electrode with the patient's skin and applying low-frequency electric current. Another one is arranged to apply a weak magnetic field to the skin by means of ultra short wave. On the other hand, in the field of acupuncture and moxibustion, in order to obtain therapeutic and pain-killing effects, physical stimulation is applied to a patient by inserting a needle or burning moxa on reactive electro-permeable points (REPP) or so-called "Tsubo" (Japanese) of a human body. Herein, the REPP are generally located by an expert on the basis of long experience and perception. Also, it is well known that the resistance at REPP is decreased as compared with other points and that the passage of electric current;through the body increases. Accordingly, by utilizing this information, the search and location of REPP can be implemented. On the other hand, although it is expected that the remedial effect will be increased by simultaneously applying a physical stimulation and a thermal stimulation on REPP, it is extremely difficult to simultaneously and quickly apply both the physical stimulation and the thermal stimulation using conventional techniques. Also, it is difficult to partially apply the thermal stimulation in a deep portion of an REPP.

SUMMARY OF THE INVENTION

It is an object of the present invention to provide a method and apparatus of increasing the curing effect by simultaneously and quickly applying both physical therapeutic/ remedial and thermal stimulation to reactive electro-permeable points of a human body.

A first aspect of the present invention resides in a method of applying high-frequency current to reactive electro-permeable points of a patient, the method comprising the steps of: applying DC electric current between first and second electrodes; connecting the second electrode to a wrist of a patient; moving the first electrode over a patient's skin to locate a reactive electro-permeable points of the patient; inserting an acupuncture needle at the detected reactive electro-permeable point; contacting the first electrode with the acupuncture needle; and applying a high-frequency wave current between the first and second electrodes for a predetermined time.

A second aspect of the present invention resides in an apparatus of applying high-frequency wave to reactive electro-permeable points of a patient comprising first and second electrodes; means for generating high-frequency wave current; means for generating direct current; means for outputting the high-frequency wave current from the high-frequency wave current generating means to the first and second electrodes for a predetermined time; means for switchingly connecting the first and second electrodes with one of said means for generating the high-frequency wave current and the means for outputting the high-frequency current for a predetermined time; and means for indicating a magnitude of the direct current which flows between the first and second electrodes when the high-frequency wave current generating means is connected with the first and second electrodes.

BRIEF DESCRIPTION OF THE DRAWINGS

FIGS. 3A and 3B show detailed perspective views of the electrode of the apparatus according to the present invention; and FIGS. 4A, 4B, 4C and 4D show thermographs which show changes of temperature of patient body surface after applied medical treatment according to the present invention.

DETAILED DESCRIPTION OF THE INVENTION

Referring to FIGS. 1 to 4D, there is shown an embodiment of a method and apparatus of applying a high-frequency wave to reactive electro-permeable points of patients according to the present invention.

Figure 1:
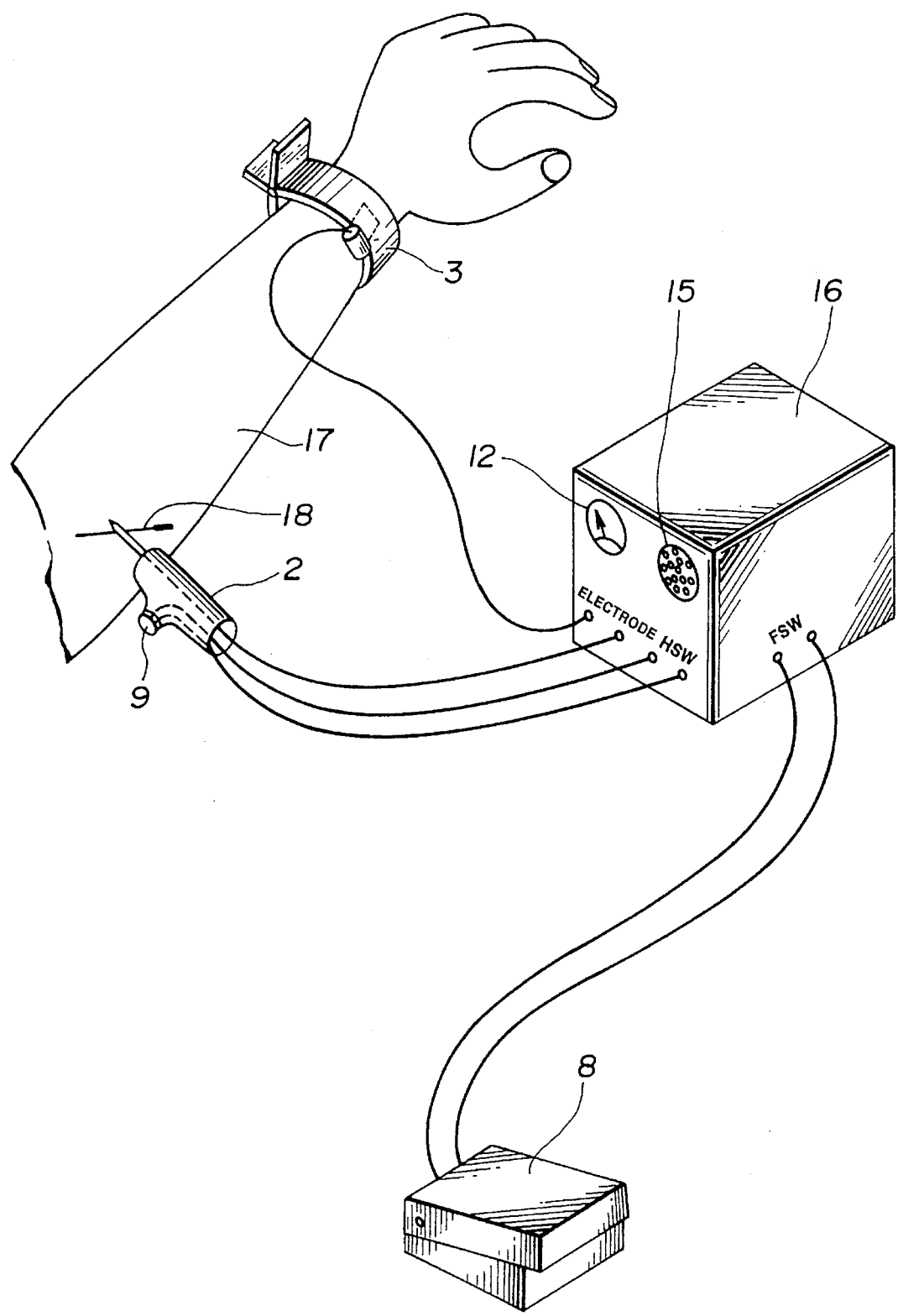
FIG. 1 is a perspective view of an embodiment of an apparatus according to the present invention.
Figure 2:
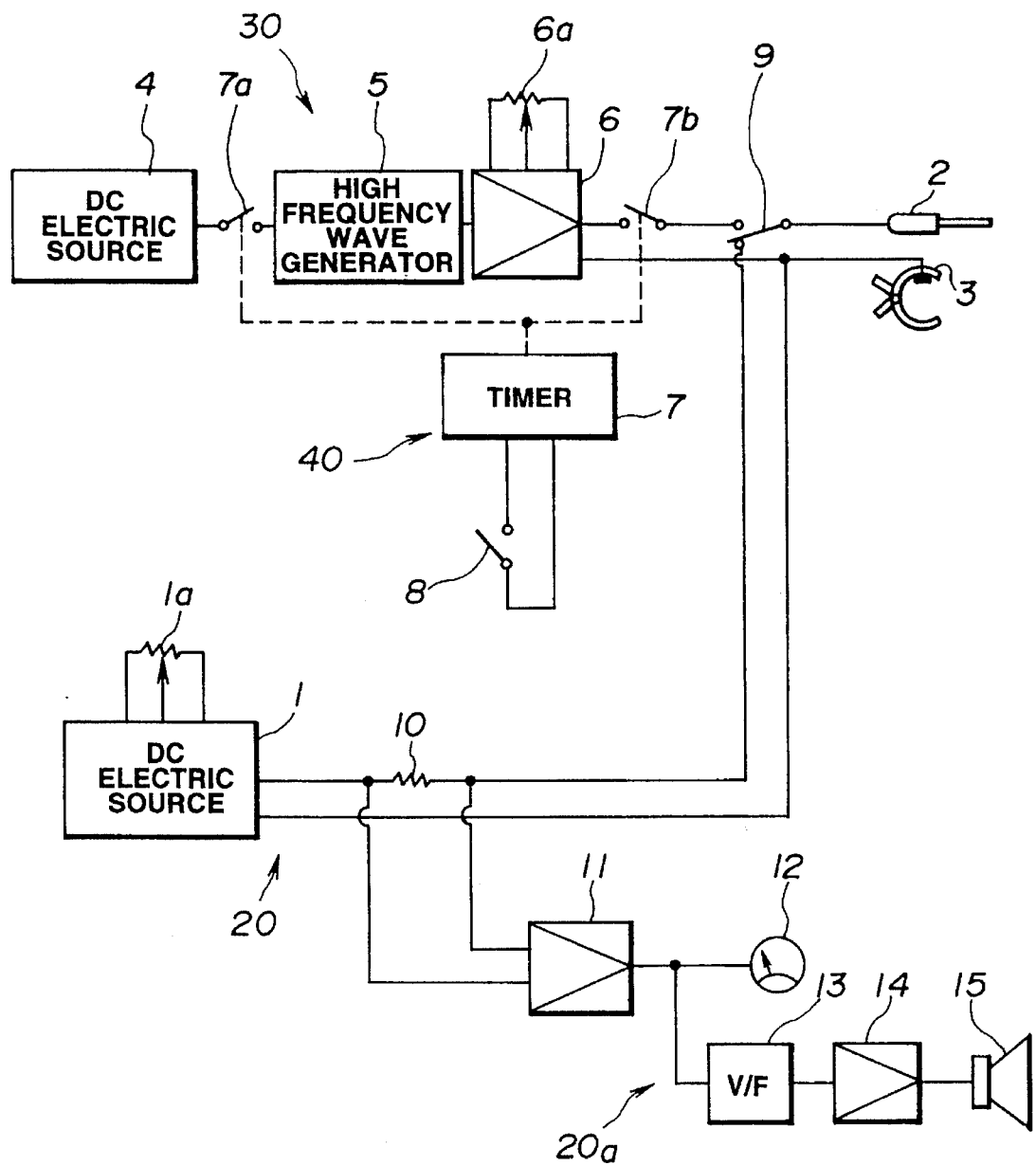
FIG. 2 is a structural view which shows an embodiment of the present invention.

As shown in FIGS. 1 and 2, the apparatus according to the present invention comprises a set of first and second electrodes 2 and 3. The first electrode 2 is formed in a handy stick or probe shape and is used for locating reactive electro-permeable points (REPP) and applying high-frequency wave current to the REPP through an acupuncture needle 18. The second electrode 3 takes the form of a clamp which can be clamped on a wrist of the patient. The first and second electrodes 2 and 3 are connected to a REPP searching device 20 and a high-frequency wave current generating device 30 through a selector switch 9.

The REPP searching device 20 comprises a DC electric source 1 which includes a variable resistor 1a for variably setting the magnitude of the output of the DC electric current and an alarm device 20a which is arranged to inform the REPP by detecting changes of DC electric current passing a resistor 10 between the first and second electrodes 2 and 3 set on the patient body 17. The alarm device 20a comprises a resistor 10 for detecting DC electric current passing between the first and second electrodes 2 and 3. One side, for example, a plus electrode side of the output of the DC electric source 1 is connected to a terminal of a normal close side of the handy selector switch 9 through the resistor 10 for detecting the direct-current electric current, and the other side of the output (in this case, a negative electrodes side) is connected to the second electrode 3. Both ends of the resistor 10 are connected to an amplifier circuit 11 for amplifying the change of the DC electric current passing the resistor 10. The amplified DC electric signal is applied to a meter 12 which informs as to whether the first electrode 2 is in contact with a REPP or not. Further, the amplifier circuit 11 is connected with a speaker 15 through a voltage/ frequency converter (V/F converter) 13 and an amplifier circuit 14. Accordingly, the speaker 15 is arranged to output a sound which changes level according to the change of the resistance between the first and second electrodes 2 and 3. In this embodiment, the speaker 15 is arranged to output a high tone sound when the electrodes 2 is in contact with a REPP.

The high-frequency wave current generating device 30 comprises a DC electric source 4 for generating DC electric current. The DC electric source 4 is connected to a high-frequency wave generator 5 for generating a high-frequency wave of about 2–20 MHz. The high-frequency wave generator 5 is connected to a variable amplifier circuit 6 including a variable resistor 6a for variably changing the magnitude of the high-frequency wave to about 0.5–7W.

A high-frequency wave control switching device 40 is arranged to manually turn on the supplement of high-frequency wave to the patient and to automatically turn off the supplement of the high-frequency wave after a predetermined time. The high-frequency wave control switching device 40 includes a first switch 7a connecting the DC electric source 4 and the high-frequency wave generator 5, and a second switch 7b connecting the amplifier circuit 6 and a normal open side of the selector switch 9. The first and second switches 7a and 7b are controlled by a foot switch 8 and a timer 7. The first and second switches 7a and 7b are turned on when the foot switch 8 is manually turned on, and are turned off after a desired time period set at the timer 7, such as 1–10 seconds has elapsed. The timer switches 7a and 7b may be replaced by a semiconductor switch which operates similarly.

The REPP searching device 20 and the high-frequency wave current generating device 30, shown schematically in FIG. 2, are housed in an apparatus body 16 shown in FIG. 1. The foot switch 8, the selector switch 9 and the first and second electrodes 2 and 3 are connected to connector terminals of the apparatus body 16. The meter 12 and the speaker 15 are attached on a panel surface of the apparatus body 16.

As shown in FIG. 3A, the first electrode 2 is formed by a grip portion 2a and a bar-shaped tip 2b. The tip 2b is of about 2–5 mm diameter and is detachably screwed into the grip portion. FIG. 3B shows a deformation of the first electrode 2 which includes a roller holder 2c and a roller 2d instead of the tip 2b. The roller 2d is formed to have several hundreds projections through which high-frequency wave current is applied to the patient skin and is directly rolled on the patient's skin.

The manner of operation of this embodiment of the medical care apparatus according to the present invention will be discussed hereinafter.

First, the second electrode 3 is clamped on a wrist of a patient and the tip end of the first electrode 2 is applied to the skin in an area where it is assumed that a given REPP exists. When the tip end of the first electrode 2 reaches the REPP, the resistance of the human body between the first and second electrodes 2 and 3 assumes a small value, and therefore the direct current flowing between the first and second electrodes 2 and 3 increases. The increase of the direct current flow can be noted from that the variation of the meter 12 indicates a peak value or that the sound from the speaker 15 is changed into a higher sound. Also, by indicating the increase of the direct current as a resistance change of the human body upon inverting the detected signal, it may be arranged such that the deflection of the meter 12 is changed into a smaller value or that the sound from the speaker 15 is changed into a lower sound.

Next, an acupuncture needle 18 made of a stainless steel wire of about 0.2 mm diameter is inserted into the REPP. Then, the first electrode 2 is contacted with the conductive portion of the needle 18 while the selector switch 9 is kept turned on. By pushing the conveniently located selector switch 9, the first electrode 2 is switched to the high-frequency side, and then by pushing the foot switch 8, high-frequency wave current flows the human body 17 between the acupuncture needle 18 and the second electrode 3 for a preset time of the timer 7 such as 1–10 seconds. The high-frequency wave current generates heat in the vicinity of the acupuncture needle 18 due to the induction heating function.

With the thus arranged apparatus according to the present invention, it becomes possible to rapidly locate REPP and obtain both of the physical medical care effect of the acupuncture and the thermal medical care effect at the deep point of the inserted needle for a short time such as about 1–10 seconds.

Although a high-frequency wave current is effective within the range of 2–10 MHz, the range from several hundreds kHz to 40 MHz is available. Electrical shock occurs below several hundred MHz, and above 40 MHz wave current can not flow due to the increases resistance of the human body. Hitherto, it has not been considered to use the high-frequency wave current for an application to the acupuncture. However, as a result of the experiment, it was confirmed that if a high-frequency wave of about 0.5–7 W was used for about ten seconds, no danger was caused, and a remarkable pain-killing effect with an attendant hemokinesis acceleration was obtained.

The electrode 2 may be formed into a clip structure which is able to clamp the acupuncture needle 18. Also, as a second electrode 3, a sheet-shaped electrode or plate-shaped electrode formed by a conductive rubber, resin or metal may be used and wound or attached to a hand, a foot, a back or an abdomen of the patient. Although in the above-mentioned embodiment in order to output high-frequency for a predetermined time the reliability is improved by arranging such that both of the electric source supply side to the high-frequency generating circuit 5 and the output side of the amplifier circuit 6 are arranged to be turned on/off at the timer contact-points 7a and 7b, either of them may be omitted principally. For the REPP search, for example, a tactual device such as a vibrator may be used as means for indicating the detected DC current others than a visible meter or the like and an audible device such as a speaker may be used. Furthermore, a resistor for protection may be added to a DC current output side and a high-frequency output side of the REPP search as a safety measure. If such a measure is employed, the output limiting function of the dc electric source 1 and the amplifier circuit 6, which is provided for safety, may be omitted or facilitated. Thus, the present invention can be applied in various ways and can take various forms.

As is clear from the above explanation, according to the acupuncture using high frequency wave of the present invention, it becomes possible to quickly locate REPP on the human body and to simultaneously and quickly apply physical stimulation and the thermal stimulation to the REPP at a relatively deep depth. This enables increase of the remedial effect.

DATA

FIGS. 4A to 4D show thermographs which show an experimental data of the medical care according to the present invention. This experiment was carried out as follows: (1) inserting the acupuncture needles at four points which are located at right and left hand side points at 1.5 cm distance from each spinous process of the fifth and sixth cervical vertebra (C-5 and C-6) in right and lift hand sides, and (2) applying high-frequency wave current to the acupuncture needles.

Figure 4A:
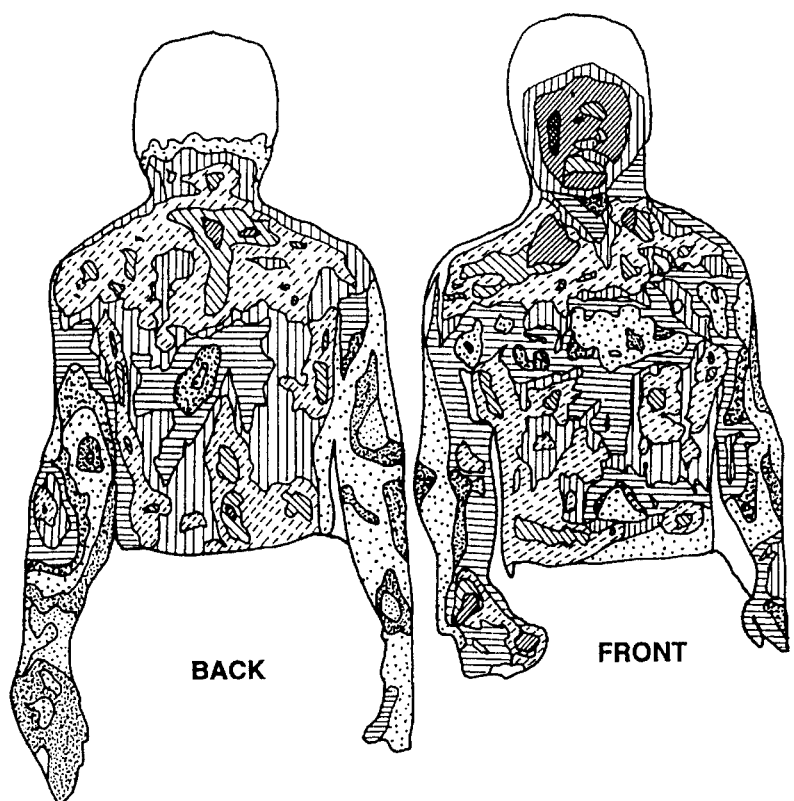
Figure 4B:
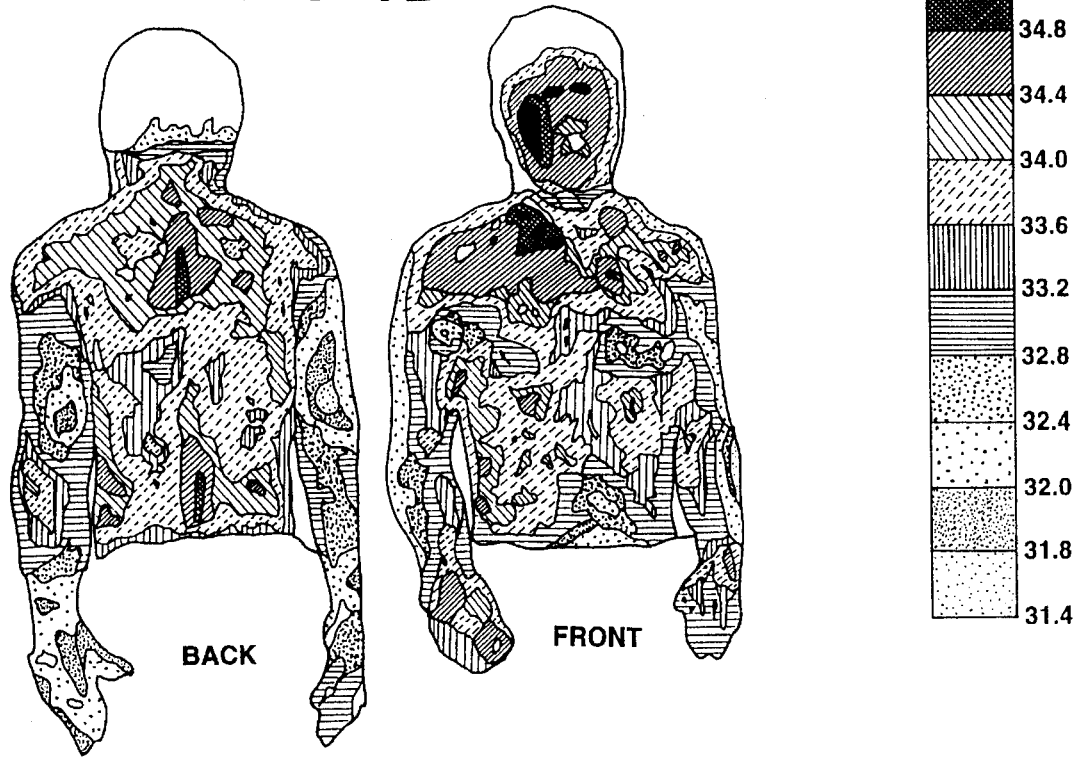

FIG. 4A is a thermograph showing an initial body surface temperature condition of a patient, FIG. 4B shows the body surface condition that a period of 20 minutes has elapsed after the treatment, FIG. 4C shows the body surface condition after a period of 40 minutes has elapsed following the treatment, and FIG. 4D shows the body surface condition after a period of 90 minutes has elapsed after the treatment. As is clear from the comparison of the thermographs of FIGS. 4A to 4D, the temperature of the body surface of the patient gradually increased. Especially, temperature increase is generated in portions of the hands. This indicates that the treatment accelerated hemokinesis.

On the other hand, for about three months, the medical treatment by the method according to the present invention was experimentally applied to 235 patients having lumbago, to 114 patients having suffering of a neck and to 13 patients having arthralgia of a knee. As a result of this treatment, 186 of 235, 82 of 114 and 9 of 13 respectively, exhibited good progress and/or recovery. This treatment is applied to light cases once a week and to serious cases twice or third times a week. These results were deemed indicative that the treatment was effective.

What is claimed is:

1. A method of applying high-frequency current to reactive electro-permeable points of a patient, the method comprising the steps of:

connecting a first electrode to a wrist of a patient;

applying DC electric current between the first electrode and a second electrode;

moving the second electrode over the patient's skin in a manner to detect a reactive electro-permeable point on the patient;

inserting an acupuncture needle at the detected reactive electro-permeable point;

connecting the second electrode with the acupuncture needle; and applying a high-frequency wave current which is controlled within 2–10 MHz and within 0.5–7 W output to the acupuncture needle through the first and second electrodes for a period automatically limited to 1–10 seconds.

2. A method as claimed in claim 1, wherein the second electrode is formed in a handy stick shape.

3. An apparatus for applying a high-frequency wave to a reactive electro-permeable point of a patient, comprising:

an acupuncture needle which is inserted into a body of the patient at the reactive electro-permeable point;

first and second electrodes, said first electrode being connected to the body of the patient and said second electrode being connected to said acupuncture needle;

means for generating high-frequency wave current;

means for generating DC electric current;

means for outputting the high-frequency wave current from said high-frequency wave current generating means to said first and second electrodes for a predetermined time;

means for switchingly connecting said first and second electrodes with one of said means for generating DC electric current and said means for outputting high-frequency current; and means for indicating a magnitude of DC electric current which flows between the first and second electrodes when said DC electric current generating means is connected with said first and second electrodes;

wherein said high-frequency wave current outputting means outputs the high-frequency current between said first electrode connected to the body of the patient and the second electrode connected to the acupuncture needle and wherein the acupuncture needle is inserted at a point whereat the magnitude of said DC electric current maximizes.

4. An apparatus as claimed in claim 3, wherein said outputting means includes a timer circuit which is triggered in response to a manually generated signal and which determines said predetermined time and for limiting the time for which high-frequency current is output to said first and second electrodes.

5. An apparatus as claimed in claim 4, wherein said timer circuit is arranged so that said predetermined time is in the range of 1–10 seconds.

6. A method of applying high-frequency current to reactive electro-permeable points of a patient, the method comprising the steps of:

connecting a wrist electrode to a wrist of a patient;

applying DC electric current between a wrist electrode and a roller electrode;

rolling the roller electrode on the patient's skin and detecting a reactive electro-permeable point of the patient;

applying a high-frequency wave current controlled within 2–10 Mhz and with 0.5–7 W output between the wrist electrode and the roller electrode; and rolling the roller electrode in the vicinity of the detect reactive electro-permeable point.

7. A method of applying high-frequency current to reactive electro-permeable points of a patient, the method comprising the steps of:

attaching a wrist electrode of a high-frequency current applying means on a wrist of the patient;

inserting an acupuncture needle at a predetermined reactive electro-permeable point of the patient;

contacting a stick-type electrode of the high-frequency current applying means with the acupuncture needle; and applying a high-frequency wave current controlled within 2–10 MHz and within 0.5–7 W output to the acupuncture needle through the first and second electrodes for for an automatically controlled period of 1–10 seconds.

8. An apparatus for applying high-frequency wave current to reactive electro-permeable points of a patient, comprising:

first and second electrodes to be attached on a body of the patient;

means for generating high-frequency wave current; and means for producing localized heating of a reactive electro-permeable point on a patient by outputting the high-frequency wave current from said high-frequency wave current generating means to said first and second electrodes; and timer means for limiting the period of time for which the high-frequency wave current is output to said first and second electrodes to a predetermined short time.

9. A method of applying high-frequency current to reactive electro-permeable points of a patient, the method comprising the steps of:

connecting a wrist electrode of a high-frequency current generating means to a wrist of a patient;

applying a high-frequency wave current between the wrist electrode and a roller electrode;

rolling the roller electrode of the high-frequency current generating means in the vicinity of a reactive electro-permeable point of the patient; and limiting the time for which the high-frequency wave current is applied to the wrist electrode and the roller electrode to a predetermined number of seconds.

10. An method as claimed in claim 9, wherein said step of rolling induces heating of the reactive electro-permeable point.

11. A method as claimed in claim 9, wherein said predetermined number of seconds is selected to be between 1 and 10 seconds.

12. An apparatus for applying high-frequency wave to a reactive electro-permeable point on a patient, comprising:

an acupuncture needle inserted into the reactive electro-permeable point;

a first electrode electrically connected to a predetermined portion of a patient's body remote from said reactive electro-permeable point;

a second electrode electrically connected to said acupuncture needle;

first current generating means for generating high-frequency wave current;

second current generating means for generating DC electric current;

means for selectively switching the connection between said first and second electrodes and said first and second current means; and timer means for automatically limiting the time for which high-frequency wave current is permitted to be continuously supplied to said first and second electrodes from said first current generating means and cause heating of said acupuncture need.

13. An apparatus comprising:

a source of DC current;

a first electrode which is electrically connected with said source of DC current and which can be attached to a predetermined portion of a body of a patient;

a hand-held unit;

a second electrode which is electrically connected with said source of DC current, said second electrode forming part of said hand-held unit in a manner which enables the second electrode to slide over the skin of a patient in manner which allows a point whereat the amount of DC current which flows between said first and second electrodes maximizes to be determined and locate a reactive electro-permeable point on a patient;

a source of high-frequency wave current;

a selector switch mounted on said hand-held unit, said selector switch being operable to switch connection between said first and second electrodes from said source of DC current to said source of high-frequency wave current;

a second manually operable switch; and timer means responsive to said second manually operable switch for enabling high energy wave current to be supplied to said first selector switch for a predetermined short period of time.

14. An apparatus as claimed in claim 13, further comprising an acupuncture needle with is inserted into the body of the patient at the reactive electro-permeable point detected using said second electrode, and wherein said hand-held unit is arranged to provide an electrical connection between said second electrode and said acupuncture needle.

15. A method of detecting and treating reactive electro-permeable points on a patient comprising the steps of:

detecting a reactive electro-permeable point on a patient's body by detecting the maximization of a DC current flow between a first electrode which is held in a predetermined fixed position against the patient's body and a second movable electrode which is adapted to be slid over the patient's body;

inserting an acupuncture needle at the detected reactive electro-permeable point to induce physical stimulation of the electro-permeable point;

connecting the second electrode to the acupuncture needle; and applying a high-frequency wave current to the acupuncture needle in a manner to cause heating of the acupuncture needle and deep non-superficial thermal stimulation of the electro-permeable point.

* * * * *